(12) United States Patent
Andjelic

(10) Patent No.: US 8,349,354 B2
(45) Date of Patent: Jan. 8, 2013

(54) COMPOSITE LAYERED HEMOSTASIS DEVICE

(75) Inventor: Sasa Andjelic, Nanuet, NY (US)

(73) Assignee: Ethicon, Inc., Somerville, NJ (US)

( * ) Notice: Subject to any disclaimer, the term of this patent is extended or adjusted under 35 U.S.C. 154(b) by 468 days.

(21) Appl. No.: 12/564,298

(22) Filed: Sep. 22, 2009

(65) Prior Publication Data

US 2011/0070288 A1  Mar. 24, 2011

(51) Int. Cl.
*A61F 13/00* (2006.01)
*A61L 15/00* (2006.01)
*C08G 63/02* (2006.01)
*C08G 63/66* (2006.01)

(52) U.S. Cl. ........ 424/443; 424/445; 424/446; 424/447; 424/486; 424/487; 528/272; 528/300

(58) Field of Classification Search .................. None
See application file for complete search history.

(56) References Cited

U.S. PATENT DOCUMENTS

| | | |
|---|---|---|
| 3,364,200 A | 1/1968 | Ashton et al. |
| 3,997,512 A | 12/1976 | Casey et al. |
| 4,080,969 A | 3/1978 | Casey et al. |
| 4,626,253 A | 12/1986 | Broadnax, Jr. |
| 5,002,551 A | 3/1991 | Linsky et al. |
| 5,007,916 A | 4/1991 | Linsky et al. |
| 5,180,398 A | 1/1993 | Boardman et al. |
| 6,500,777 B1 | 12/2002 | Wiseman et al. |
| 7,238,850 B2 | 7/2007 | Shimanuki |
| 7,279,177 B2 | 10/2007 | Looney et al. |
| 2004/0005350 A1 | 1/2004 | Looney et al. |
| 2005/0113849 A1 | 5/2005 | Popadiuk et al. |
| 2006/0051398 A1 | 3/2006 | Andjelic et al. |
| 2006/0257457 A1 | 11/2006 | Gorman et al. |
| 2006/0258995 A1 | 11/2006 | Pendharkar et al. |
| 2007/0100271 A1 | 5/2007 | Shimanuki |
| 2007/0149640 A1 | 6/2007 | Andjelic et al. |
| 2008/0103284 A1 | 5/2008 | Andjelic |
| 2008/0254091 A1 | 10/2008 | Lee et al. |
| 2009/0104276 A1 | 4/2009 | Andjelic et al. |
| 2009/0118241 A1 | 5/2009 | Andjelic et al. |

OTHER PUBLICATIONS

Andjelic, et al 'Hydrophilic Absorbable Copolyester Exhibiting Zero-Order Drug Release' (2006) Pharmaceutical Research. vol. 23 No. 4 pp. 821-834.
International Search Report re: PCT/US2010/48336 dated Apr. 15, 2011.

*Primary Examiner* — Marsha Tsay
(74) *Attorney, Agent, or Firm* — David R. Crichton

(57) ABSTRACT

The present invention is directed to a hemostatic composite structure having a bioabsorbable fabric or non-woven substrate having at least two major oppositely facing surface areas and a continuous non-porous polymer-based film that is laminated on one major surface of said substrate. The bioabsorbable fabric substrate can be an oxidized polysaccharide and/or the non-woven substrate can be made from bioabsorbable, non-cellulosic derived polymers. The continuous non-porous polymer based film can be a bioabsorbable polymer. The present invention also relates to a method for providing hemostasis by applying a composite structure described herein onto a wound site in need of a hemostatic device wherein a major surface of the substrate without the film layer is applied onto the wound site.

16 Claims, 4 Drawing Sheets

ized fabric on one side with a continuous, non-porous polymer-based film. The composite structure of fabric or non-woven substrate and the continuous, non-porous polymer-based film provides significantly better hemostasis performance than the fabric or non-woven substrate alone. More specifically, the hemostatic composite structure of the current invention has minimal loft (low profile), and the polymeric film has a low softening or melting point to allow lamination at relatively low processing temperatures.

COMPOSITE LAYERED HEMOSTASIS DEVICE

FIELD OF THE INVENTION

The present invention relates to a multilayered hemostatic composite structure. The present invention relates to a hemostatic composite structure containing a fabric or non-woven substrate laminated on one side with a continuous, non-porous polymer-based film. The composite structure of fabric or non-woven substrate and the continuous, non-porous polymer-based film provides significantly better hemostasis performance than the fabric or non-woven substrate alone. More specifically, the hemostatic composite structure of the current invention has minimal loft (low profile), and the polymeric film has a low softening or melting point to allow lamination at relatively low processing temperatures.

BACKGROUND OF THE INVENTION

The control of bleeding is essential and critical in surgical procedures to minimize blood loss, to reduce post-surgical complications, and to shorten the duration of the surgery in the operating room. Due to its biodegradability and its bactericidal and hemostatic properties, cellulose that has been oxidized to contain carboxylic acid moieties, hereinafter referred to as carboxylic-oxidized cellulose, has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures.

Currently utilized hemostatic wound dressings include knitted or non-woven fabrics comprising carboxylic-oxidized cellulose. Currently utilized oxidized regenerated cellulose (ORC) is carboxylic-oxidized cellulose comprising reactive carboxylic acid groups and which has been treated to increase homogeneity of the cellulose fiber. Examples of such hemostatic wound dressings commercially available include Surgicel® absorbable hemostat; Surgicel Nu-Knit® absorbable hemostat; and Surgicel® Fibrillar absorbable hemostat; all available from Johnson & Johnson Wound Management Worldwide, a division of Ethicon, Inc., Somerville, N.J., a Johnson & Johnson Company. Other examples of commercial absorbable hemostats containing carboxylic-oxidized cellulose include Oxycel® absorbable cellulose surgical dressing from Becton Dickinson and Company, Morris Plains, N.J. The oxidized cellulose hemostats noted above are knitted fabrics having a porous structure effective for providing hemostasis. They exhibit good tensile and compressive strength and are flexible such that a physician can effectively place the hemostat in position and maneuver the dressing during the particular procedure being performed.

Published U.S. Patent application No. 2006/051398 describes the fully amorphous copolymers of poly(ethylene diglycolate) (PEDG) and glycolide for use as films in adhesion prevention formulations. The application is silent with the regard of using this film in combination with hemostasis products to achieve enhanced hemostasis performance.

U.S. Pat. No. 6,500,777 describes a method for forming an ORC (oxidized regenerated cellulose) multilayered film for use as an adhesion prevention barrier comprising a cellulose film with cellulose fabric (sandwiched between films) followed by oxidation of multi-layered film. The film is placed on both sides of ORC Fabric. The cellulose film, subject to further oxidization, is not of a continuous, non-porous polymer-based film. In addition, the intended use of the device is for adhesion prevention, and is silent for use in hemostasis.

Published US Patent application No. 2008/0254091 describes a multi-layered adhesion prevention barrier comprising a nanofibrous electrospun layer coated on both side with hydrophilic non-synthetic, bio-originated polymer film. This device is intended for adhesion prevention. The reference is silent about the hemostasis use which does address the specific sidedness of the polymeric film.

U.S. Pat. No. 7,238,850 describes a multi-layered multi-function hemostasis tool for stopping bleeding by absorbing blood from the wound, which includes a lamination comprising a water-permeable inner material on the wound side, a water-impermeable outer material on the side departing from the wound side, a pulp-cotton laminated body between the inner and outer materials, a crust between the pulp-cotton laminated body and the water-impermeable outer material for diffusing the blood that has passed through the water-permeable inner material and the pulp-cotton laminated body, and a polymer for absorbing the blood diffused by the crust. However, the reference is silent on having a top, non-porous, continuous film layer made from amorphous or low crystallinity absorbable polymers.

Published US Patent Application No. 2005/0113849 describes a prosthetic repair device comprising a non-absorbable material, a first absorbable material having a first absorption rate and a second absorbable material having a faster absorption rate than the first absorption rate. Alternatively, the non-absorbable material is encapsulated with a first absorbable component having a first absorption rate. The device, having a non-absorbable component, is intended for hernia repair procedures and is silent for the use as a hemostatic device.

Published US Patent Application No. 2006/0257457 is directed to a method of making a reinforced absorbable multilayered hemostatic wound dressing comprising a first absorbable non-woven fabric, a second absorbable woven or knitted fabric, including also a thrombin and/or fibrinogen as a hemostatic agents. The reference is silent on having a non-porous, continuous film component.

U.S. Pat. No. 7,279,177 B2 assigned to Ethicon is directed to a hemostatic wound dressing that utilizes a fibrous, fabric substrate made from carboxylic-oxidized cellulose and containing a first surface and a second surface opposing the first surface, the fabric having flexibility, strength and porosity effective for use as a hemostat; and further having a porous, polymeric matrix substantially homogeneously distributed on the first and second surfaces and through the fabric, the porous, polymeric matrix being made of a biocompatible, water-soluble or water-swellable cellulose polymer, wherein prior to distribution of the polymeric matrix on and through the fabric, the fabric contains about 3 percent by weight or more of water-soluble oligosaccharides. The reference is silent on having a non-porous, continuous film.

Decreasing the time to achieve hemostasis has great clinical significance—to save blood loss and speed up the procedure. The majority of current products on the market in case of mild to moderate bleeding achieve hemostasis in a time frame from about 4 to 8 minutes. In addition, many products do not have ideal handling characteristics as they wrinkle and fold during surgical procedures especially in the presence of blood or other fluids. A medical needs remains for hemostatic devices that have better mechanical properties, particularly for use in laparoscopic procedures. Finally, some products when used in multiple layers or those in particulate form may disintegrate or their parts may migrate during the application process. There is a clear medical need to achieve faster hemostasis to reduce blood loss during surgery as well as a desire to provide improved handling performance and an improved ability to stay in place after application.

SUMMARY OF THE INVENTION

The present invention provides a hemostatic composite structure comprising fabric or non-woven substrate, laminated on one side with a continuous, non-porous polymer-based film. The composite structure of the fabric or non-woven substrate and continuous, non-porous polymer-based film provides significantly better hemostasis performance than ORC or non-ORC substrates alone. Advantageously, the device of the current invention should have minimal loft (low profile), and the polymeric film should have a low softening or melting point to allow lamination at relatively low processing temperatures. Furthermore, the continuous, non-porous polymeric film component (absorbable or non-absorbable), may be designed to additionally provide tissue support, help in wound healing, act as a drug (active) delivery carrier, etc.

The present invention is directed to a hemostatic composite structure having a bioabsorbable fabric or non-woven substrate having at least two major oppositely facing surface areas and a continuous non-porous polymer-based film that is laminated on one major surface of said substrate. The bioabsorbable fabric substrate can be an oxidized polysaccharide and/or the non-woven substrate can be made from bioabsorbable, non-cellulosic derived polymers. The continuous non-porous polymer based film can be a bioabsorbable polymer, such as a bioabsorbable polymer selected from the group consisting of poly(ethylene diglycolate-co-glycolide), poly (ethoxyethylene diglycolate-co-glycolide), poly(lactide), poly(glycolide), poly(p-dioxanone), poly(ε-caprolactone), poly(hydroxybutyrate), poly(b-hydroxybutyrate), poly(hydroxyvalerate), poly(trimethylene carbonate), poly(tetramethylene carbonate), poly(amino acids) and copolymers and terpolymers thereof.

In one embodiment, the substrate contains oxidized regenerated cellulose and the continuous non-porous, top coat film is a copolymer comprising poly(ethylene diglycolate-co-glycolide).

In another embodiment, the thickness of the substrate is from 0.05 to 0.75 mm and the density of the substrate is from 0.05 to 0.6 g/cm3. In another embodiment, the thickness of the substrate is from about 0.05 to 2 mm. In still another embodiment, the density of the substrate is from 0.05 to 0.25 g/cm3. In still another embodiment, the film has a thickness in the range of about 0.5 to 2 mils.

The hemostatic composite structure can optionally further include a bioactive agent, such as a hemostatic agent, including hemostatic agents selected from the group consisting of procoagulant enzymes, proteins and peptides, prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above and any combination thereof. In one embodiment, the hemostatic agent is selected from the group consisting of thrombin, fibrinogen and fibrin.

In one embodiment, the film layer is made from a polymer material that is fully amorphous or semi-crystalline absorbable polymers. In another embodiment, the film layer is made from a polymer material having a melting point temperature below 120° C., more preferably less than 110° C. In another embodiment, the film layer is made from a polymer material having a glass transition temperature of less than about 25° C.

The present invention also relates to a method for providing hemostasis by applying a composite structure described herein onto a wound site in need of a hemostatic device wherein a major surface of the substrate without the film layer is applied onto the wound site.

DETAILED DESCRIPTION OF THE INVENTION

Figure 1:
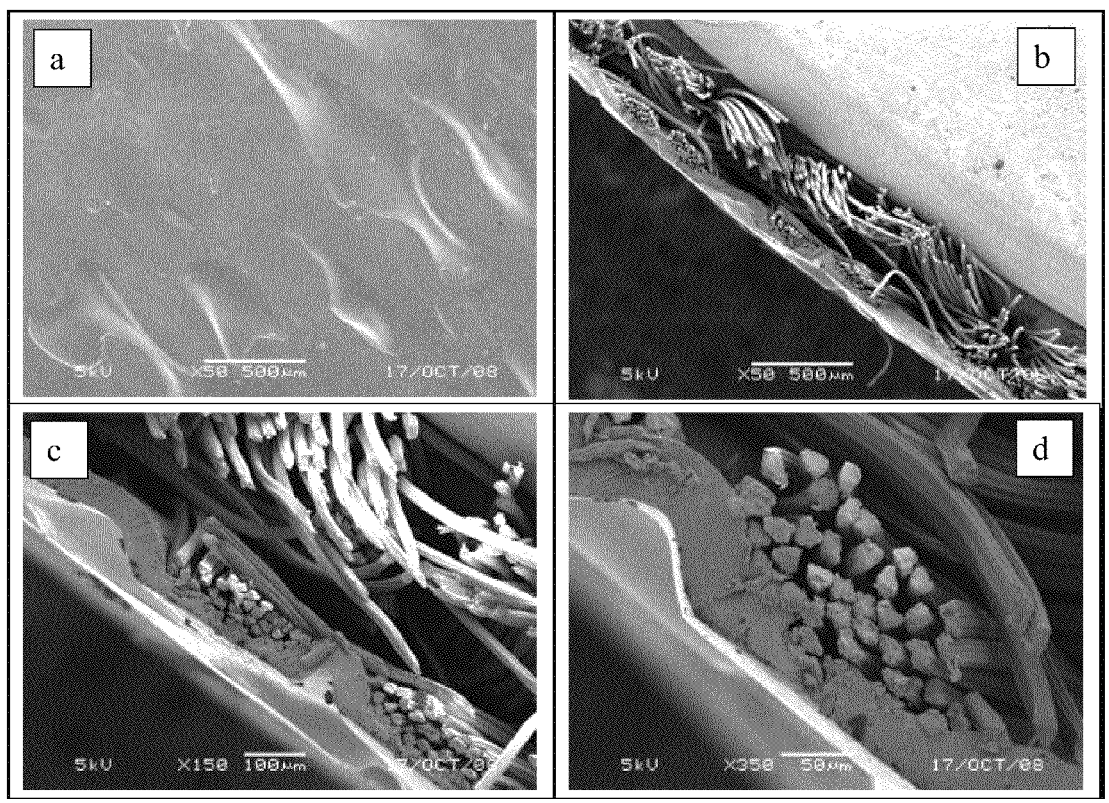
FIG. 1a is a scanning electron microscopy image (×50) of a top view of a fabric substrate laminated with a 2-mil polymeric film
FIG. 1b is a scanning electron microscopy image (×50) of a cross section of a fabric substrate laminated with a 2-mil polymeric film
FIG. 1c is a scanning electron microscopy image (×150) of a cross section of a fabric substrate laminated with a 2-mil polymeric film
FIG. 1d is a scanning electron microscopy image (×350) of a cross section of a more dense fabric substrate laminated with a 2-mil polymeric film

Applicants discovered a certain hemostatic composite structure described more fully below that utilizes a fabric or non-woven material as a substrate, where the fabric or non-woven substrate comprises fibers prepared from a biocompatible and biodegradable polymer(s) and a continuous, non-porous polymer film layer. The substrate surface opposite the polymer film layer is applied to the wound surface. The composite structure described below possesses properties suitable for use as a hemostat, e.g. strength, and flexibility. The hemostatic composite structure of the present invention provides and maintains effective hemostasis when applied to a wound requiring hemostasis. Effective hemostasis, as used herein, is the ability to control and/or abate capillary, venous, or arteriole bleeding within an effective time, as recognized by those skilled in the art of hemostasis.

The composite structure described below provides improved hemostasis, meaning decreasing the time to achieve hemostasis, which has great clinical significance. It will be shown that the present invention provides much improved hemostasis rates over conventional hemostats.

The composite structure described below exhibits better handling properties for surgical applications and settings. Many fabric or non-woven based hemostats do not have ideal handling characteristics as they wrinkle and fold during surgical procedures especially in the presence of blood or other fluids. The substrate/film composites of the present invention minimize such behavior. Additionally, the presence of film improves the mechanical strength and pliability of the fabric or non-woven substrate based materials, enhancing their suitability for use in laparoscopic procedures. In laparoscopic procedures, the composite is expected to be pushed through the trocar and sprung open into the body cavity more easily than either the substrate or film components individually.

The composite structure described below exhibit greater propensity and/or ability to stay in place during surgical procedures relative to existing hemostatic devices. For example, some fabric based products when used in multiple layers, or those in non-woven form may disintegrate or their parts may migrate during the application process. A substrate/film composite architecture of the present invention helps to maintain the physical integrity of the hemostatic materials, so it cannot fall prematurely to pieces, curve, or migrate during the procedure. Another advantage of the composite structure is that the device can be sutured in place.

The composite structure device of the present invention also provides for the potential to use the film component for additional surgical functionality, such as to provide tissue support, to help in wound healing and/or to act as delivery carrier for bioactive agents.

As noted above, hemostatic composite structure of the present invention comprise a fabric or non-woven substrate on the first, wound contacting surface of the hemostatic composite structure, laminated with a continuous, non-porous polymer-based film on second surface of the hemostatic composite structure. Substrate as used herein refers to the component of the hemostatic composite structure which is in direct contact to the wound surface. The substrates utilized in the present invention may be fabric/woven or nonwoven that provides form and shape and mechanical reinforcement necessary for use in hemostatic composite structures. In addition, the substrates are made of materials having hemostatic properties and be bioabsorbable.

Bioabsorbable, "Biodegradable" and "bioabsorbable" as used herein refer to a material that is broken down spontaneously and/or by the mammalian body into components, which are consumed or eliminated in such a manner as not to interfere significantly with wound healing and/or tissue regeneration, and without causing any significant metabolic disturbance.

Polymers useful in preparing the fabric or non-woven substrates in hemostatic composite structure of the present invention include, without limitation, collagen, calcium alginate, chitin, polyester, polypropylene, polysaccharides, polyacrylic acids, polymethacrylic acids, polyamines, polyimines, polyamides, polyesters, polyethers, polynucleotides, polynucleic acids, polypeptides, proteins, poly(alkylene oxide), polyalkylenes, polythioesters, polythioethers, polyvinyls, polymers comprising lipids, and mixtures thereof. Preferred fibers comprise oxidized regenerated polysaccharides, in particular oxidized regenerated cellulose.

Preferably, oxidized polysaccharides are used to prepare wound dressings of the present invention. More preferably, oxidized cellulose is used to prepare fabrics used in wound dressings of the present invention. The cellulose either may be carboxylic-oxidized cellulose, or may be aldehyde-oxidized cellulose, each as defined and described herein. Even more preferably, oxidized regenerated cellulose is used to prepare fabric substrates used in wound dressings of the present invention. Regenerated cellulose is preferred due to its higher degree of uniformity versus cellulose that has not been regenerated. Regenerated cellulose and a detailed description of how to make regenerated oxidized cellulose is set forth in U.S. Pat. No. 3,364,200 and U.S. Pat. No. 5,180,398, the contents each of which is hereby incorporated by reference as if set forth in its entirety. As such, teachings concerning regenerated oxidized cellulose and methods of making same are well within the knowledge of one skilled in the art of hemostatic wound dressings.

Substrates, or fabrics utilized in conventional hemostatic wound dressings, such as Surgicel® absorbable hemostat; Surgicel Nu-Knit® absorbable hemostat; and Surgicel® Fibrillar absorbable hemostat; all available from Johnson & Johnson Wound Management Worldwide, a division of Ethicon, Inc., Somerville, N.J., a Johnson & Johnson Company, as well as Oxycel® absorbable cellulose surgical dressing from Becton Dickinson and Company, Morris Plains, N.J., all may be used in preparing wound dressings according to the present invention. In certain embodiments, wound dressings of the present invention are effective in providing and maintaining hemostasis in cases of severe bleeding. As used herein, severe bleeding is meant to include those cases of bleeding where a relatively high volume of blood is lost at a relatively high rate. Examples of severe bleeding include, without limitation, bleeding due to arterial puncture, liver resection, blunt liver trauma, blunt spleen trauma, aortic aneurysm, bleeding from patients with over-anticoagulation, or bleeding from patients with coagulopathies, such as hemophilia. Such wound dressings allow a patient to ambulate quicker than the current standard of care following, e.g. a diagnostic or interventional endovascular procedure.

The fabric substrates utilized in the present invention may be woven or nonwoven, provided that the fabric possesses the physical properties necessary for use in hemostatic wound dressings. A preferred woven fabric has a dense, knitted structure that provides form and shape for the hemostatic wound dressings. Such fabrics are described in U.S. Pat. No. 4,626,253, U.S. Pat. No. 5,002,551, and U.S. Pat. No. 5,007,916, the contents of which is hereby incorporated by reference herein as if set forth in its entirety.

The nonwoven substrates may be produced by melt-blown, electrospinning, needle punched methods and they can be preferably made from absorbable polymers. More specifically, absorbable nonwoven fabric is comprised of fibers that are not derived from cellulosic materials, such as comprising aliphatic polyester polymers, copolymers, or blends thereof. The aliphatic polyesters are typically synthesized in a ring opening polymerization of monomers including, but not limited to, lactic acid, lactide (including L-, D-, meso and D, L mixtures), glycolic acid, glycolide, $\epsilon$-caprolactone, p-dioxanone (1,4-dioxan-2-one), and trimethylene carbonate (1,3-dioxan-2-one). Examples of non-woven substrates are described in published U.S. patent application No. 2009/0104276 and published U.S. patent application No. 2006/0258995, the contents of which are hereby incorporated by reference herein as if set forth in their entireties.

Other methods known for the production of nonwoven fabrics may be utilized and include such processes as air laying, wet forming and stitch bonding.

The thickness of the substrate ranges from about 0.05 to 2 mm, preferably from 0.25 to 0.75 mm. The thickness is measured according to ASTM method (D1777-64) conventionally used for the textile industry in general and non-woven in particular. The fabric density of the substrate ranges from about 0.05 to 0.6 g/cm$^3$; preferably from 0.15 to 0.5 g/cm$^3$. The fabric density is defined as the ratio of the fabric's base weight to the fabric's thickness. Base weight is defined as the weight of the 1 cm by 1 cm square piece fabric.

Other fabric constructions which produce equivalent physical properties may, of course, be utilized in the manufacture of the improved fabric or non-woven substrate and hemostatic composite structure of the present invention, and such constructions will be apparent to those skilled in the art.

As noted above, hemostatic composite structure of the present invention comprise a continuous, non-porous polymer film laminated on the surfaces of the fabric or non-woven substrate of the second and the wound opposing surface of the hemostatic composite structure. Having a polymeric film on the second and wound opposing surface provide additional mechanical barriers to prevent the blood leaking from the wound once hemostasis is initially achieved. The preferred polymeric films according to the invention are fully amorphous or semi-crystalline absorbable polymers of relatively low melting point temperature (below 120° C., more preferably less than 110° C.) allowing the use of low processing temperatures, which greatly help in keeping the substrate materials free of degradation. Also, polymer films of the current invention need to have relatively low (around room temperature 25° C. or below) glass transition temperatures as measured by differential scanning colorimetry for the hemostatic composite to be soft, pliable and conformable to the tissue or body contour.

The polymers used to prepare the laminated film in wound dressings of the present invention are preferably biocompatible synthetic absorbable polymers. More preferably, the polymers of the current inventions are fully amorphous (0% crystallinity) or low melting semi-crystalline polymers to allow processing (lamination) conducted at relatively low temperatures for purposes as described above. This is important because ORC-based substrates can degrade during exposure at higher temperatures for instance, 100° C. for the time duration of lamination process. Even more preferably, the polymer films need to have relatively low glass transition temperatures (e.g. room temperature or lower) to be soft, flexible, elastic, to drape and conform well to the body and tissues. Even more preferably the polymer films needs to absorb/hydrolyze relatively quickly; for instance, about two to four weeks, which is slightly longer than the absorption rate of ORC-based substrate, but still fast to aid in patient comfort and to limit possible long-term infections. Finally, in case polymer films are laminated onto ORC-based substrate, polymer films of the current invention needs to exhibit minimal degradation upon gamma or e-beam irradiation procedures at sufficient levels, such as about 10-40 kGy, to sterilize the composite structure and optionally the associated packaging.

The thickness of the film can vary and does not appear to have a significant effect on hemostasis performance. Nonetheless, if the film is too thin, the improvement in mechanical strength of the composite structure relative to the substrate alone is negligible. On the other hand, if the film layer is too thick, the composite structure is too stiff and difficult to handle. Applicants found that a preferred polymer film thickness ranges from 0.5 to 2 mils (1 mil=in/1000).

Preferred polymers used to laminate the substrate include, the polymers and copolymers of poly(ethylene diglycolate) (PEDG), poly(ethoxyethylene diglycolate) (PEEDG), glycolide, lactide, p-dioxanone, caprolactone, trimethylene carbonate and derivatives of any of the above. Examples of such absorbable polymers are taught in published US Patent Application No. 2009/0118241, published U.S. patent application No. 2009/0104276, published U.S. Patent No. 2008/0103284, published U.S. patent application No. 2007/0149640 A1, the disclosure of each of which is incorporated by reference.

The first absorbable nonwoven fabric is attached to the second absorbable woven or knitted fabric, either directly or indirectly. For example, the polymer film may be incorporated into the absorbable woven or knitted fabric via thermal lamination (calendaring), needle punching, embossing or by chemical or thermal bonding. More preferably, the hemostatic composite device of the current invention may be made, for example, by contacting an one side of the substrate (ORC or nonwoven) with a film, and heating the substrate and the film so that a portion of the substrate is adhered to the film component.

More specifically, a hemostatic composite device of the current invention can be prepared utilizing a lamination system having a metal roller with a nominal diameter of 8 inches and a heating capability of is up to 170° C. The rotating speed of the metal roller can vary from 1 to 10 feet per minute. The lamination system also included a soft face polyurethane pressure roller with a durometer of 40 and a pressure loading of up to 150 pounds per linear foot. One side of a film can be covered with a first silicone based release paper while the other side of the film can be placed in contact with the one side of a substrate. A second release paper was placed on the top side of the substrate to keep the components from sticking to the rollers of the lamination system. The first release paper/film/substrate/second release paper structure can be placed into the lamination system with the metal roller set to a temperature of 50-120° C. and running at 1 to 2 feet per minute. Meanwhile, the pressure roller can be set to apply a load of 70 pounds per linear inch displaced across the face of the pressure roller, with the first release paper contacting the heated metal roller, which can forced the small portion of the film surface to migrate into the substrate. See, for instance, SEM Images of various hemostatic composites in FIGS. 1-3.

Generally, higher temperatures and/or slower roller speed allow more of the film to penetrate into the substrates, making the adherence much stronger. When an ORC substrate is used, it is important to keep the metal roller temperature as low as possible to avoid degradation of ORC component. Therefore, fully amorphous, or semi-crystalline film with low melting point and relatively low glass transition temperature as discussed above are preferable to use for this procedure.

In certain embodiments of the invention, the hemostatic composite structure may further include a hemostatic agent, or other biological or therapeutic compounds, moieties or species, including drugs and pharmaceutical agents as described in more detail herein below. The agents may be bound within the polymeric matrix, as well as to the fabric surfaces and/or within the fabric. The agents may be bound by chemical or physical means, provided that they are bound such that they do not migrate from the wound dressing upon contact with blood in the body. The hemostatic agent may be dispersed partially or homogenously through the fabric and/or the polymeric matrix. In some embodiments of the invention, the hemostatic agents, or other biological or therapeutic compounds, moieties or species, e.g. drugs, and pharmaceutical agents, may be "acid-sensitive", meaning that they may be degraded or denatured by, or otherwise detrimentally affected by acidic pH, such as is provided by conventional carboxylic-oxidized hemostatic wound dressings.

Hemostatic agents that may be used in hemostatic composite structure according to the present invention include, without limitation, procoagulant enzymes, proteins and peptides, can be naturally occurring, recombinant, or synthetic, and may be selected from the group consisting of prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above and any combination thereof. Preferred hemostatic agents used in the present invention are thrombin, fibrinogen and fibrin.

Such hemostatic composite structure of the present invention comprises hemostatic agents, including but not limited to thrombin, fibrinogen or fibrin, in an amount effective to provide rapid hemostasis and maintain effective hemostasis in cases of severe bleeding. If the concentration of the hemostatic agent in the wound dressing is too low, the hemostatic agent does not provide an effective proagulant activity to promote rapid clot formation upon contact with blood or blood plasma. The agents may be incorporated into either the substrate or film components.

The laminated hemostatic composite structure described herein may be used as an adjunct to primary wound closure devices, such as arterial closure devices, staples, and sutures, to seal potential leaks of gasses, liquids, or solids as well as to provide hemostasis. For example, the multilayered dressing may be utilized to seal air from tissue or fluids from organs and tissues, including but not limited to, bile, lymph, cerebrospinal fluids, gastrointestinal fluids, interstitial fluids and urine. The laminated hemostasis device described herein has additional medical applications and may be used for a variety of clinical functions, including but not limited to tissue reinforcement and buttressing, i.e., for gastrointestinal or vascular anastomoses, approximation, i.e., to connect anastomoses that are difficult to perform (i.e. under tension), and tension releasing. The dressing may additionally promote and possibly enhance the natural tissue healing process in all the above events. This dressing can be used internally in many types of surgery, including, but not limited to, cardiovascular, peripheral-vascular, cardio-thoracic, gynecological, neuro- and general surgery. The dressing may also be used to attach medical devices (e.g. meshes, clips and films) to tissues, tissue to tissue, or medical device to medical device.

Figure 2:
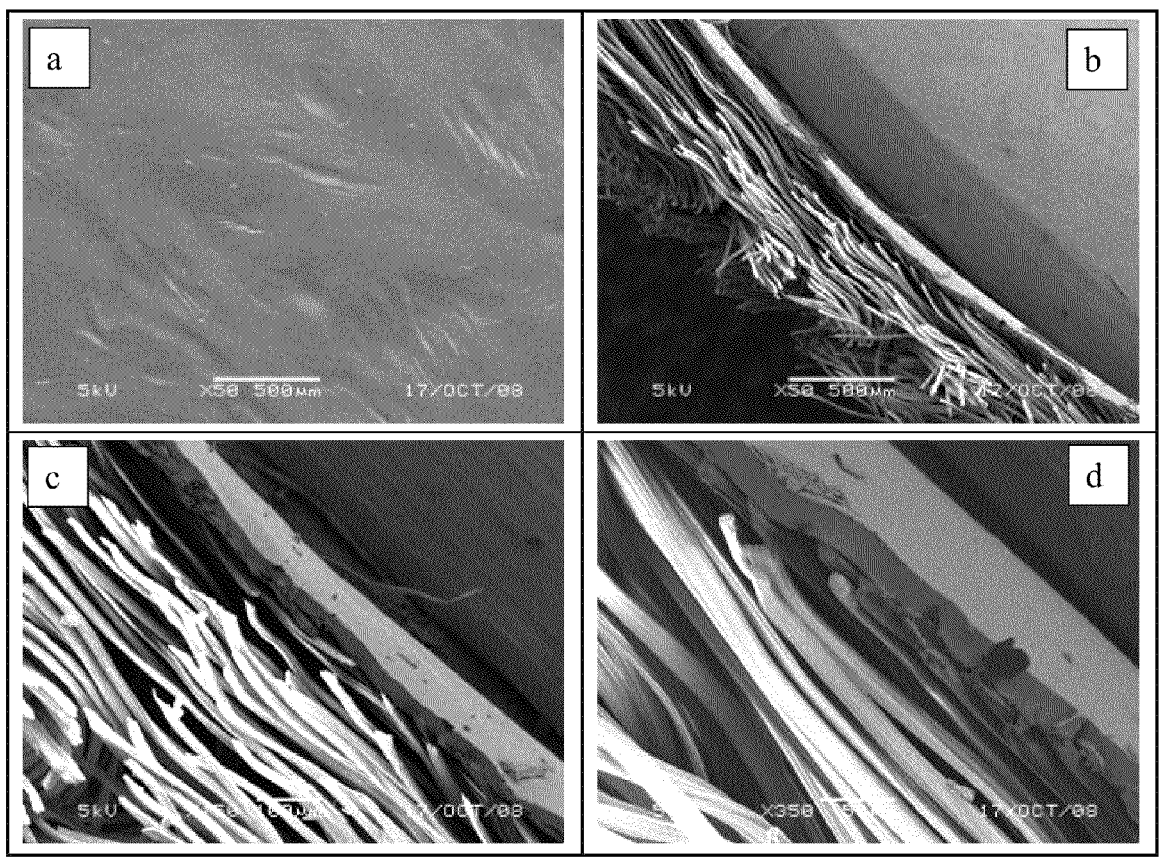
FIG. 2a is a scanning electron microscopy image (×50) of a top view of a more dense fabric substrate laminated with a 1-mil polymeric film
FIG. 2b is a scanning electron microscopy image (×50) of a cross section of a more dense fabric substrate laminated with a 1-mil polymeric film
FIG. 2c is a scanning electron microscopy image (×150) of a cross section of a more dense fabric substrate laminated with a 1-mil polymeric film
FIG. 2d is a scanning electron microscopy image (×350) of a cross section of a more dense fabric substrate laminated with a 1-mil polymeric film
Figure 3:
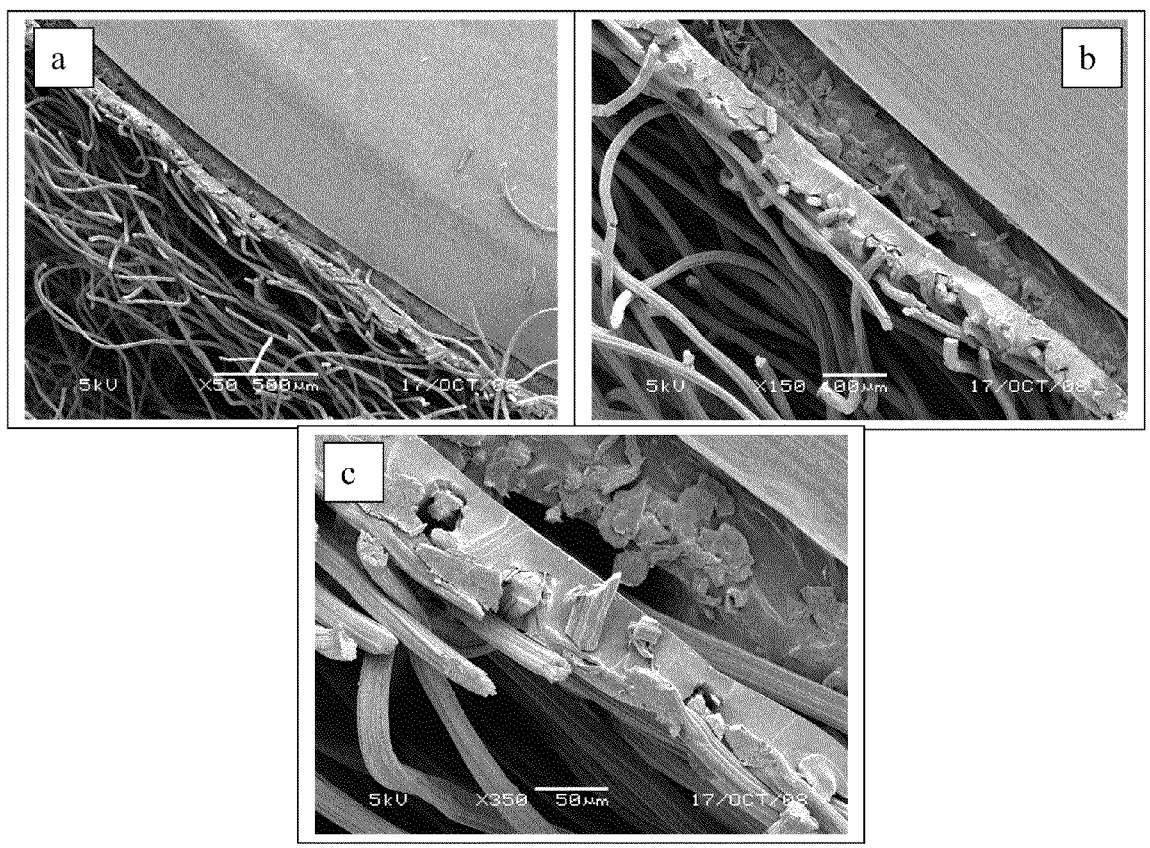
FIG. 3a is a scanning electron microscopy image (×50) of a cross section of a non-woven substrate laminated with a 2-mil polymeric film
FIG. 3b is a scanning electron microscopy image (×150) of a cross section of a non-woven substrate laminated with a 2-mil polymeric film
FIG. 3c is a scanning electron microscopy image (×350) of a cross section of a non-woven substrate laminated with a 2-mil polymeric film

Hemostatic composite structure of the present invention is best exemplified in the figures prepared by scanning electron microscope. The samples were prepared by cutting 1-cm$^2$ sections of the dressings by using a razor. Micrographs of both the first surface and opposing second surface, and cross-sections were prepared and mounted on carbon stubs using carbon paint. The samples were gold-sputtered and examined by scanning electron microscopy (SEM) under high vacuum at 4 KV. The SEM images of different substrate/polymer film combinations are shown in FIGS. 1-3.

While the following examples demonstrate certain embodiments of the invention, they are not to be interpreted as limiting the scope of the invention, but rather as contributing to a complete description of the invention.

Example 1

(First Stage of the Polymer Film Starting Material) Synthesis of Hydroxy Terminated Poly(Ethylene Diglycolate) (PEDG)

A twin-agitated reactor with intermeshing patterned blades equipped with a condenser is employed to prepare a polycondensation product of diglycolic acid and ethylene glycol using dibutyltin oxide as catalyst. After charging the reactor with 7.0 kg of diglycolic acid, 9.7 kg of ethylene glycol and 1.30 grams of dibutyltin oxide catalyst, the pressure in reactor is lower to 1 Torr or less and held overnight. The next day, the vacuum is released with dry nitrogen/argon. Vessel oil temperature was set to 170° C., condenser water was set to 1-2 GPM, and the upper/lower condenser heats is set to 95° C./50° C. The agitator is set at 30 RPM in reverse rotation. When the temperature in the reactor reached 150° C., the agitator speed is increased to 75 RPM and switched to forward rotation. The reaction is carried out at 170° C. for a couple hours until approximately all water is distilled and/or first traces of ethylene glycol appeared in the distillate. At this point the first nitrogen/argon stage is completed; pressure is lowered gradually to full vacuum in steps while the temperature of the batch is maintained at 175-180° C. Using Brookfield melt viscometer, a viscosity of the hydroxy end-capped polymer is checked periodically to ensure the end product of specific molecular weight. After sufficient reaction time spent under vacuum (68 hours, final vacuum reading 150-200 mTorr) the reaction is stopped and the material sent for analysis. It was a fully amorphous, colorless viscous liquid with a glass transition temperature of about 0-2° C. Weight average molecular weight is 19,000 g/mol; the resin exhibited an inherent viscosity (IV) of 0.62 dL/g, as determined in HFIP at 25° C. at a concentration of 0.1 g/dL. The resin is kept in the reactor under nitrogen/argon until the next, copolymerization stage.

Example 2

(Second Stage of the Polymer Film Starting Material) the Copolymerization of an α,ω-Dihydroxy Poly(Ethylene Diglycolate) Homopolymer with Glycolide, PEDG/Gly The hydroxy terminated poly(ethylene diglycolate) (PEDG) remained in the reactor (7.7 kg) was reacted with glycolide monomer (10.3 kg) in the second stage via ring-opening polymerization. The reactor is equipped with a melt tank reservoir allowing glycolide monomer to be added in a liquid state. Before charging glycolide, a vacuum of less than 1 Torr is kept overnight to remove any residual moisture. The next day, the resin is heated to about 150° C., at which point the molten glycolide monomer is transferred from the melt tank with agitation. Agitator mixing is continued (20 RPM) and the batch temperature raised to 150° C. until full mixing is achieved. In situ, a real-time Fourier transform near-infrared probe is used to confirm complete mixing of components before the addition of the catalyst, Stannous Octoate (1.12 ml of toluene solution, glycolide to catalyst level 240,000:1). Temperature is then increased to 210° C. and the reaction was continued for another two hours. A half an hour before discharging, a vacuum is pulled slowly (step by step) to remove any residual monomer. The discharged copolymer is fully amorphous, with a colorless to slightly yellow tint, and a glass transition temperature of 25.5° C. Weight average molecular weight was 35,000 g/mol and an inherent viscosity of 1.09 dL/g, as determined in HFIP at 25° C. at a concentration of 0.1 g/dL, was recorded. Composition is confirmed by NMR to be 42/58 by weight poly(ethylene diglycolate-co-glycolide). Melt index measurements revealed MI=0.152 g/10 min @ 150° C. using load of 3700 grams.

The discharged copolymer resin is kept in the freezer until the grinding step. After grinding, the resin is placed in port-a-vacs (capacity 4-5 kg) and stored under vacuum in the refrigerator cabin (temperature set at 10° C.). After two weeks under vacuum, the resin is ready for further processing (extrusion).

Example 3

Film Extrusion of PEDG/Gly 42/58 wt. % Copolymer

Film extrusion of the copolymer described in Example 2 is performed on Davis-Standard Extruder (Model KN125, Pawcatuck, Conn., USA) using a 6-inch die with die gap of 6 mils. Extruder temperature ranged from 125° C. in Barrel Zone 1 to 150° C. in Barrel Zone 3, with the sheet die temperature set at 155° C. Extruder pressure (barrel) is controlled between 2000 and 2500 psig. Screw rotation speed varied from 7.5 to 17.9 rpm. Upstream, middle, and downstream rolls are all kept at ambient conditions with Silicone based release paper employed to prevent the extruded, warm film of sticking to rolls.

Extruded films with the thicknesses of 1 and 2 mills are kept in-between released paper and stored under the vacuum. Unless specified, there is one layer of substrate used in the hemostatic composite structure.

Example 4

Preparation of Hemostatic Composite Structures Having ORC Substrates and PEDG/Gly 42/58 wt % Copolymer Composites Films made from PEDG/Gly 42/58 wt. % copolymer resin having thickness of 1 and 2 mil are laminated on a variety of ORC based substrates, available from Ethicon Inc., under the tradename of Surgicel Classic®, (Examples 4A) and (4A'; 2 layers), Surgicel NuKnit®, (Example 4B), Surgicel Fibrillar®, (Example 4C), as well as a nonwoven construct made from ORC (Example 4D) using J. J. Jenkins (Matthews, N.C., USA) heating set of Godets with the nipping roll combination. Laminations are successfully done at various Godet's temperatures ranging from 50 to 90° C. Fully amorphous copolymer films allow the use of low processing temperatures, which greatly help in keeping the ORC materials free of degradation. The roll speed used is generally 1 FPM for 2-mil films and 2 FPM for 1-mil films. Produced composites exhibit excellent handling properties, and no delamination of films are observed in any of the prepared combinations. SEM images presented in FIGS. 1-3 show films embedded (melted) into the portions of fibers on the surface of fabrics making the very strong bond. The largest improvement in handling properties are observed for Example 4A' with 2-mil film—no delamination of the second layer or wrinkling of the fabric is observed; in the case of Example 4C,—no disintegration, or breaking up of individual parts of fabric was noted since the film keeps them together effectively. Also, in the case of wet environment, the side laminated with film can be easily handled since the film surface is not sensitive to moisture/water presence. After lamination procedure, film/ORC substrate composites are placed in-between silicone release paper and stored in the vacuum chamber until further use.

Example 5

Preparation of Hemostatic Composite Structures Having Non-ORC Substrates and PEDG/Gly 42/58 wt % Copolymer Composites Various non-ORC substrates are laminated using PEDG/Gly 42/58 film as a top-coat. These non-woven substrates include combination substrate, poly(glycolide-co-lactide) (PLGA, glycolide90/lactide10 mol/mol) nonwoven Fabric needled-punched with ORC fabric as described in published U.S. patent application No. 2006/0258995, (Examples 5A and 5A'), poly(glycolide-co-lactide) (PLGA, glycolide90/lactide10 mol/mol) nonwoven Fabric, (Example 5B) and melt blown non-woven 25/75ε-caprolactone/glycolide copolymer, as described in published U.S. patent application No. 2009/0104276 having two different thicknesses (Examples 5C and 5C'), and a Surgifoam, absorbable gelatin sponge (Example 5D). The lamination conditions in all these cases are the same to those in Example 4 as described above. Good handling with no delamination is observed in all of the non-ORC composites.

Example 6

Preparation of Hemostatic Composite Structures Having ORC Substrates and PDS Film Composites Films made from undyed poly(p-dioxanone) PDS resins having thickness of 0.8 mil are laminated on a variety of ORC based substrates, available from Ethicon Inc., under the tradename of Surgicel Classic®, (Examples 6A) and (6A'; 2 layers), and Surgicel NuKnit®, (Example 6B), Laminations are successfully done at roll temperature of 120° C. This processing temperature is higher than in the case of fully amorphous films described in previous examples (Examples 4 and 5) because PDS film is semi-crystalline material with the melting point of about 110° C. The roll speed used for lamination of 0.8-mil undyed PDS film is kept at 2 FPM. Produced composites exhibit good handling properties, especially under dry conditions. In the case of wet environment, the film side can be easily handled since the film surface is not sensitive to water presence. However, the film compliance in the wet field is not as good as in the case of PEDG/Gly 42/58 film. Due to its semi-crystalline morphology, the PDS film tends to curve slightly upon application. PDS film/ORC composites are placed in-between silicone release paper and stored in the vacuum chamber until further use.

Example 7

Evaluation of Hemostatic Composite Structures Having Film/ORC Substrates and Film/Non-ORC Substrates Using Swine Linear Incision Spleen Model Linear incision on a standard swine spleen model, 1.5 cm long and 3 mm deep is used to generate hemostasis data for various test articles prepared as described in Examples 4-6. The depth of each wound is kept constant by clamping the scalper blade in a pair of needle holders at the appropriate depth. The first wound at the distal end of the spleen serves as a negative control and was permitted to bleed for a minimum 10 minutes to demonstrate the bleeding potential of an untreated wound. The second wound is made approximately 1 cm proximal to the first incision. This and the 10-18 subsequent incisions (the number depending on the size of the pig) per each test animal are used as the test incisions.

After the incision is created, the test articles (approximately 1.5 cm×2.5 cm) are applied with slight pressure using gauze over the incision line and a stopwatch was started. At the end of tamponade time of 2 minutes, the pressure is released. The gauze is removed and wound inspected for any sign of active bleeding. The procedure is repeated following approximately 30 seconds intervals until the bleeding (hemorrhage) completely stopped. The time of the last release of pressure is recorded as the time to achieve hemostasis. Each test articles, in most cases, are applied to total 3 or 4 respective wounds.

The hemostatic composite structures having film/ORC and film/non-ORC are placed onto the wound with the substrate contacting the wound and with the film side opposing to the wound. The time of achieving hemostasis is recorded along with general observation noted on handling characteristics and ability of test articles to stay in place after the procedure is completed. The summary of hemostasis results on test articles composed of film laminated on ORC is provided in Table 1 below.

The hemostasis results on test articles composed of film laminated on combination substrate (PLGA nonwoven Fabric needled-punched with ORC Fabric), 5A and 5A', and those laminated on exclusively non-ORC substrates (5B, 5C, 5C' and 5D) are presented in Tables 2 and 3, respectively.

TABLE 1

Hemostasis data on linear incision spleen model for different Hemostatic Composite Structures having various ORC substrates laminated with absorbable top-coat films

| ORC Substrate | Substrate Alone Hemostasis time (min:sec) | | with PEDG/Gly Copolymer Top Film | | | | | with PDS Top Film | |
|---|---|---|---|---|---|---|---|---|---|
| | | | 2-mil Film | | | 1-mil Film | | 0.8-mil Film | |
| | | | Hemostasis time (min:sec) | | Reduction Time* | Hemostasis time (min:sec) | Reduction Time* | Hemostasis time (min:sec) | Reduction Time* |
| Example 4A | >10:00 (different studies on spleen model) | | 5:12 3:22 2:45 | 3:50 | >61% | | | | |
| Example 4A' | 7:30 6:49 7:03 | 7:05 | 2:00 3:00 2:50 | 2:40 | 62% | | | | |
| Example 4B | 4:37 4:45 4:02 | 4:25 | 2:00 2:00 2:58 | 2:15 | 49% | 2:00 4:30 2:00 | 2:50 | 36% | 2:00 2:00 2:00 7:45 | 3.20 | 25% |
| Example 4D | 3:50 to 5:40 (different studies on spleen model) | | 4:30 2:50 2:46 | 3:20 | 13-41% | | | | |
| Example 4C | 3:58 4:30 5:30 | 4:40 | 5:50 5:48 2:50 | 4:35 | ~0% | | | | |
| Control: 2-mil PEDG/Gly film alone | 6:00 5:00 4:45 | 5:15 | | | | | | | |

*The percent reduction in hemostasis time as compared to the Hemostat without a top-coat.

TABLE 2

Hemostasis data on linear incision spleen model for Combination Substrate without biologics and the patch with top-coat film combination.

| Substrate | Combination Substrate Alone Hemostasis time (min:sec) | with PEDG/ Gly Copolymer Top Film | | | |
|---|---|---|---|---|---|
| | | 2-mil Film | | 1-mil Film | |
| | | Hemostasis time (min:sec) | Reduction Time | Hemostasis time (min:sec) | Reduction Time |
| Example 5A (lamination on ORC side) | 3:20 to 4:00 (from different studies on spleen model) | 2:00 2:20 3:10 | 2:30 | 25-38% | |
| Example 5A' (lamination on PLGA side) | 3:20 to 4:00 (from different studies on spleen model) | | | 2:00 2:00 2:54 2:00 | 2:14 | 33-44% |

TABLE 3

Hemostasis data on linear incision spleen model for non-ORC substrates with those containing top-coat film addition.

| Non-ORC Substrates | Substrate Alone Hemostasis time (min:sec) | 2-mil Film Hemostasis time (min:sec) | 2-mil Reduction Time | 1-mil Film Hemostasis time (min:sec) | 1-mil Reduction Time |
|---|---|---|---|---|---|
| PLGA-based 2 mm thick nonwoven patch (5B) | 5:20 (from different study on the same spleen model) | | | 2:43  2:43 | 54% |
| PLGA-based 2 mm thick nonwoven patch Film side on the wound (5B) | N/A | | | 5:00  5:00 | The same as the film alone |
| Example 5C | 2:50<br>2:00<br>3:00<br>3:05 | 2:45 | | 2:00  2:25<br>2:00<br>3:15 | 13% |
| Example 5C' | 2:00<br>2:00<br>3:00 | 2:45 | | 3:00  2:45<br>2:00<br>2:00 | 0% |
| Example 5D | 2:25 (from different study on the same spleen model) | 2:00  2:00 | 17% | | |

We have unexpectedly discovered that film/substrate composites with a single and double layer of substrates require significantly less time to achieve hemostasis than in the cases when the single or double layer substrates, or 2-mil PEDG/Gly 42/58 film are used alone. As indicated in Table 1, the thickness of the film appears not to affect the hemostasis data as both 1-mil and 2-mil thick film laminated on substrates produce significant improvement. Replacing the PEDG/Gly 42/58 film with a different absorbable polymer film, such as Poly (p-dioxanone), PDS produces the same decrease in the hemostasis time.

In addition to hemostasis improvement, hemostatic composites structures having substrates laminated with PEDG/Gly 42/58 film exhibit much better handling characteristics and ability to stay in place compared to the substrates or s the film when used alone.

On the other hand, PEDG/Gly 42/58 film laminated onto a much thicker ORC substrate e.g. Example 4C, show no significant reduction in hemostasis time when compared with the substrate alone, indicating that the thickness of ORC layer may play an important role in the hemostasis performance of the devices of the present invention.

The trend of significantly faster hemostasis is also observed for the film laminated ORC/PLGA Combination substrate presented in Table 2. Placing the film on either side of the substrate (ORC or PLGA non-woven) produced comparable results.

Finally, a series of non-ORC substrates including needle punched PLGA fiber with a gradient in fabric density (the lamination procedure was identical to those in Example 5), melt blown nonwoven ε-Cap/Gly 25/75 copolymer having two different thicknesses, and SURGIFOAM, absorbable gelatin sponge are also examined with top-coat lamination (see Table 3). Except for the thicker and denser melt blown nonwoven ε-Cap/Gly 25/75 substrate, all of them show faster hemostasis than the corresponding substrates without top-coat film.

Example 8

Determination of Base Weight and Thicknesses of ORC and Non-ORC Substrates

In order to characterize and describe various substrates used to prepare composites of the current invention, we decide to measure their base weight expressed in grams per square centimeters and the fabrics' thicknesses.

For the base weight measurements, the samples are cut into 1 cm by 1 cm pieces and weighted by an analytical balance. The thickness is measured by ASTM method ("Standard test for thickness of textile materials; Option 1", D1777) with the foot (probe) diameter of 1.1 inch and the pressure of 0.6 psi. Dividing the Base Weight, BW (g/cm$^2$) with the Thickness, T (cm) we obtain the density value for our substrates, which is another important parameter in characterizing the laminated film composites. If a substrate is too thick regardless of density, the top-coat film will not have any effect on the hemostasis time. In addition, if a substrate is relatively thick and dense the effect of top-coat film will be also negligible. The measurements of fabric base weight and thicknesses are shown in Table 4.

TABLE 4

Base weights and thicknesses of ORC and non-ORC substrates

| Substrate ID | Base Weight (g/cm$^2$) | Thickness (cm) | Density, BW/T (g/cm$^3$) |
|---|---|---|---|
| 1 - Surgicel Original one layer (Example 4As) | 0.010 | 0.025 | 0.39 |
| 2 - Surgicel Original two layers (Example 4A's) | 0.020 | 0.049 | 0.40 |
| 3 - Surgicel Nu-Knit (Example 4Bs) | 0.023 | 0.045 | 0.51 |

TABLE 4-continued

Base weights and thicknesses of ORC and non-ORC substrates

| Substrate ID | Base Weight (g/cm²) | Thickness (cm) | Density, BW/T (g/cm³) |
|---|---|---|---|
| 4 - Surgicel non-woven (Example 4Ds) | 0.011 | 0.061 | 0.16 |
| 5 - Surgicel Fibrillar (Example 4Cs) | 0.027 | 0.33 | 0.08 |
| 6 - ORC/PLGA patch (Example 5As) | 0.021 | 0.14 | 0.14 |
| 7 - PLGA based patch (Example 5B) | 0.025 | 0.14 | 0.18 |
| 8 - MB nonwoven ε-Cap/Gly 25/75 thinner substrate (Example 5C) | 0.015 | 0.47 | 0.32 |
| 9 - MB nonwoven ε-Cap/Gly 25/75 thicker substrate (Example 5C') | 0.030 | 0.90 | 0.33 |

Figure 4:
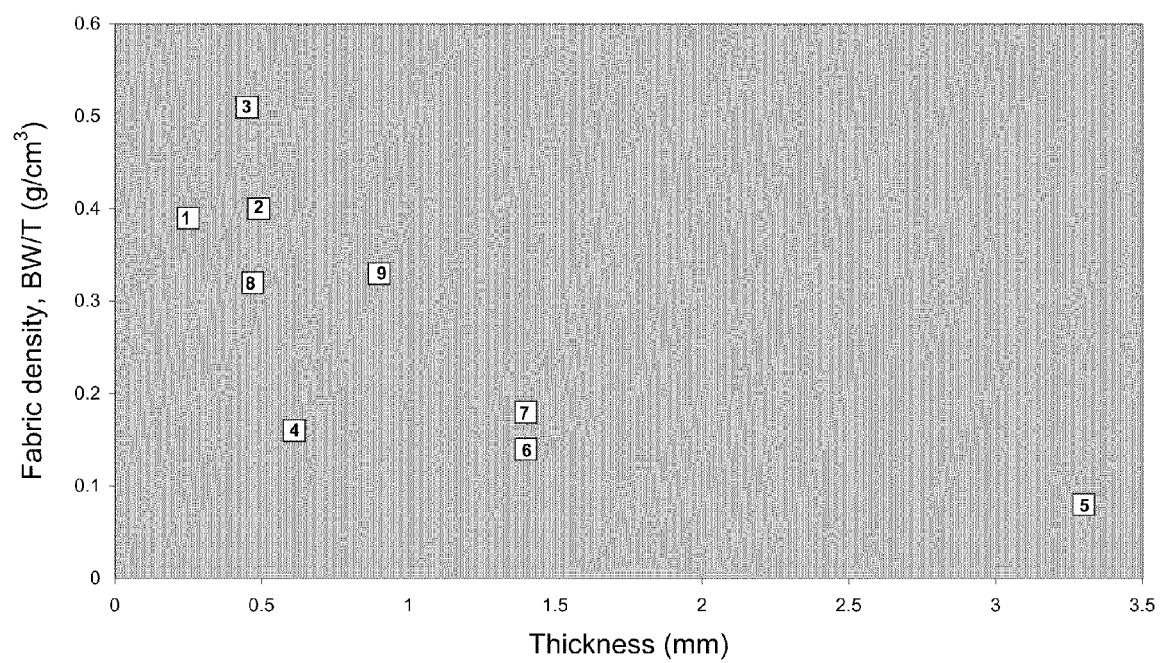
FIG. 4 is a graph showing the correlation of the hemostasis of the inventive device as a function of substrate' thicknesses and their corresponding density. The legend for the numbers on the graph is displayed in Table 4.

The plot of fabric thickness versus fabric density is displayed in FIG. 4. The two substrates that failed to produce positive hemostasis effect are marked 5 and 9 as described in Table 4.

I claim:

1. A hemostatic composite structure comprising:
   a) a bioabsorbable fabric or non-woven substrate having at least two major oppositely facing surfaces and
   b) a continuous non-porous polymer film that is laminated as a topcoat on only one major surface of said substrate.

2. The hemostatic composite structure according to claim 1 wherein the bioabsorbable fabric substrate is an oxidized polysaccharide.

3. The hemostatic composite structure according to claim 1 wherein the non-woven substrate is made from bioabsorbable, non-cellulosic polymers.

4. The hemostatic composite structure according to claim 1 wherein the continuous non-porous polymer film is a bioabsorbable polymer.

5. The hemostatic composite structure according to claim 4 wherein the bioabsorbable polymer is selected from the group consisting of poly(ethylene diglycolate-co-glycolide), poly (ethoxyethylene diglycolate-co-glycolide), poly(lactide), poly(glycolide), poly(p-dioxanone), poly(ε-caprolactone), poly(hydroxybutyrate), poly(b-hydroxybutyrate), poly(hydroxyvalerate), poly(trimethylene carbonate), poly(tetramethylene carbonate), poly(amino acids) and copolymers and terpolymers thereof.

6. The hemostatic composite structure according to claim 1 wherein the substrate contains oxidized regenerated cellulose and the continuous non-porous, polymer film is a copolymer comprising poly(ethylene diglycolate-co-glycolide).

7. The hemostatic composite structure according to claim 1, wherein the thickness of the substrate is from 0.05 to 0.75 mm and the density of the substrate is from 0.05 to 0.6 g/cm³.

8. The hemostatic composite structure according to claim 1, wherein the thickness of the substrate is from about 0.05 to 2 mm and the density of the substrate is from 0.05 to 0.25 g/cm³.

9. The hemostatic composite structure according to claim 1 further comprising a bioactive agent.

10. The hemostatic composite structure according to claim 9, wherein the bioactive agent is a hemostatic agent.

11. The hemostatic composite structure according to claim 10 wherein the hemostatic agent is selected from the group consisting of procoagulant enzymes, proteins and peptides, prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, epinephrine, selectin, procoagulant venom, plasminogen activator inhibitor, platelet activating agents, synthetic peptides having hemostatic activity, and any combination thereof.

12. The hemostatic composite structure according to claim 10 wherein the hemostatic agent is selected from the group consisting of thrombin, fibrinogen and fibrin.

13. The hemostatic composite structure according to claim 1 wherein the film layer is made from a polymer material that is fully amorphous or semi-crystalline absorbable polymers.

14. The hemostatic composite structure according to claim 1 wherein the film layer is made from a polymer material having a melting point temperature below 120° C.

15. The hemostatic composite structure according to claim 1 wherein the film layer is made from a polymer material having a glass transition temperature of less than about 25° C.

16. The hemostatic composite structure according to claim 1 wherein the film has a thickness in the range of about 0.5 to 2 mils.

* * * * *